(12) United States Patent
Welch et al.

(10) Patent No.: US 6,856,403 B1
(45) Date of Patent: Feb. 15, 2005

(54) OPTICALLY STIMULATED ELECTRON EMISSION CONTAMINATION MONITOR AND METHOD

(75) Inventors: Christopher S. Welch, Gloucester, VA (US); Daniel F. Perey, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/662,161

(22) Filed: Sep. 11, 2003

(51) Int. Cl.[7] .................................................. G01B 9/02
(52) U.S. Cl. ...................................................... 356/492
(58) Field of Search ........................... 250/306; 356/492

(56) References Cited

U.S. PATENT DOCUMENTS

| | | | |
|---|---|---|---|
| 5,393,980 A | * | 2/1995 | Yost et al. ................... 250/306 |
| 6,480,285 B1 | * | 11/2002 | Hill ............................. 356/492 |

* cited by examiner

*Primary Examiner*—John F. Niebling
*Assistant Examiner*—Andre' C. Stevenson
(74) *Attorney, Agent, or Firm*—Helen M. Galus

(57) ABSTRACT

An apparatus and method for performing quality inspections on a test surface based on optically stimulated emission of electrons. In one embodiment, the apparatus comprises a device for producing optical radiation having a plurality of different spectrum lines, selecting at least one of the spectrum lines, and directing the selected spectrum line to the test surface, and circuitry for detecting a current of photoelectrons emitted from the test surface, generating a signal indicative of photoelectron current, and for indicating a condition of quality based on the generated signal indicative of the photoelectron current. In one embodiment, the method comprises producing optical radiation having a plurality of different spectrum lines, selecting at least one of the spectrum lines and directing the selected spectrum line to the test surface, detecting a current of photoelectrons emitted from the test surface and generating a signal indicative of photoelectron current, and indicating a condition of quality based on the generated signal indicative of the photoelectron current.

31 Claims, 2 Drawing Sheets

OPTICALLY STIMULATED ELECTRON EMISSION CONTAMINATION MONITOR AND METHOD

ORIGIN OF THE INVENTION

The invention described herein was made in part by an employee of the United States Government and may be manufactured and used by and for the Government of the United States for governmental purposes without the payment of any royalties thereon or therefore.

BACKGROUND OF THE INVENTION

1. Field of the Invention

The present invention relates generally to the non-destructive evaluation of surface contamination and corrosion levels and, more particularly, to an apparatus and method for monitoring optically stimulated electron emission.

2. Description of the Related Art

Surface quality inspections are presently achieved by one of a variety of methods and techniques. One method is to omit any type of verification and just rely on tests of samples of the bonded/coated product to determine the integrity of the bond. In many cases, visual inspection for foreign particles or substances is the method of choice. In some cases, surfaces that are to be bonded are subjected to inspection by "black light" for fluorescence caused by contamination. The fluorescence occurs at visible or invisible wavelengths. A variation of the black light inspection uses fluorescence which is caused by a pulsed ultraviolet laser. Other prior art methods, such as ellipsometry, utilize changes in the direct reflected light. Another method to detect surface contaminants requires monitoring changes in infrared emissivity. These changes are sometimes emphasized by using grazing-angle infrared radiation to illuminate the sample. Methods and techniques based on reflection-infrared spectrometry are used to evaluate the chemical compounds causing the contamination.

Ionic contamination is sometimes evaluated by solvent extraction of the material from the surface of sampled product and measurement of the conductivity change of the solvent. Other contaminants are detected following solvent extraction by gravimetric measurements of non-volatile residues that remain after evaporation of the solvent in which the sample was previously immersed or washed. In another similar method, the washing solvent is passed through a filter, and the gain in weight of the filter after drying constitutes the measurement of contamination. Another method, known as the "water break test," uses the contact angle or the regularity of the edge of the solvent film as it drains from the sample under test. Another method, known as optically stimulated electron emission (OSEE), is currently being used to detect contamination. This method is described in U.S. Pat. Nos. 4,590,376 and 5,393,980. OSEE is also described in the paper by Perey, D. F., entitled "A Portable Surface Contamination Monitor Based On The Principle of Optically Stimulated Electron Emission (OSEE)," JANNAF Propulsion and Joint Subcommittee Meeting 1996, p. 8, December 1996.

If the samples of a production run are small enough, such samples can be placed in a high-vacuum system that permits a variety of methods to be used to detect and, in some cases, chemically analyze contaminants.

Another well-known technique is the use of Kelvin Probes to detect variations in the work function of samples of a production run.

Many of the previous known prior art methods are used only on production samples because these methods actually compromise (i.e. alter or damage) the sample. Thus, these methods are not used to inspect all of the production run.

Some known prior art methods, notably the solvent extraction method, require laboratory processing following the measurement process thereby increasing the processing time.

Ellipsometry is another method currently used in industry. Ellipsometry provides the best results when applied to relatively flat, smooth surfaces. However, ellipsometry does not yield highly accurate results when applied to surfaces that are not relatively flat and smooth.

Infrared methods generally have low sensitivity to small amounts of contamination but perform better when relatively high amounts of contamination are present.

The visual inspection methods, including black light inspection, can be difficult to quantify and may yield inconsistent results.

Some of these known prior art methods and techniques require fluorescent tracer materials to be added to process chemicals in order to provide the desired results.

Furthermore, only infrared reflection spectrometry and the high vacuum methods provide more than a single indicator of quality in a measurement.

Thus, it is an object of the present invention to provide an apparatus and method for performing quality inspections on a test surface that addresses the deficiencies of the known art method and apparatuses.

Additional objects and advantages of the present invention are apparent from the drawings and specification which follow.

SUMMARY OF THE INVENTION

The present invention is directed to an apparatus and method for performing quality inspections on a test surface based on optically stimulated emission of electrons. Specifically, the present invention is directed to an improvement in effecting inspections of surfaces for contamination using Optically Stimulated Electron Emission (OSEE).

Significant features of the present invention are the use of multiple measurements over the various wavelengths of light that comprise the OSEE-active portions of the incident light and the evaluation of the resulting measurements to discriminate between contamination and oxidation of the surface and among different contaminant species. Specifically, a plurality of OSEE measurements are effected on a given surface at one or more different wavelengths of incident light, and may include as well the combined wavelengths so that the comparison between the measurements can be used to distinguish between surface contamination and corrosion or oxidation and/or to distinguish among different contaminant species.

In one aspect, the present invention is directed to an apparatus for performing quality inspections on a test surface comprising a device for producing optical radiation having a plurality of different spectrum lines, selecting at least one of the spectrum lines, and directing the selected spectrum line to the test surface, and circuitry for detecting a current of photoelectrons emitted from the test surface, generating a signal indicative of photoelectron current, and indicating a condition of quality based on the generated signal indicative of photoelectron current.

In a related aspect, the present invention is directed to an apparatus for performing quality inspections on a test surface comprising a multi-state device for producing optical radiation in the direction of the test surface wherein the optical radiation defines a particular spectrum line that corresponds to a particular state of the device and wherein each state of the device effects generation of a particular spectrum line, circuitry for configuring the multi-state device into different states, and circuitry for detecting a current of photoelectrons emitted from the test surface, generating a signal indicative of photoelectron current, and indicating a condition of quality based on the generated signal indicative of photoelectron current. The condition of quality may be based on a combination of the signals indicative of photoelectron current from each state of the device. While the multi-state device can take a variety of forms, in one embodiment, the multi-state device can comprise a tunable laser wherein each state of the device corresponds to a particular wavelength to which the laser is tuned. In another embodiment, the multi-state device can comprise a filtering device that is configured to exhibit a plurality of filtering states wherein each filtering state results in only a particular spectrum line, or only a particular group of spectrum lines, to pass to the test surface. In yet another embodiment the multi-state device can comprise multiple sources of light.

In a further aspect, the present invention is directed to a method for performing quality inspections on a test surface comprising the steps of producing optical radiation having a plurality of different spectrum lines, selecting at least one of the spectrum lines and directing the selected spectrum line to the test surface, detecting a current of photoelectrons emitted from the test surface, generating a signal indicative of photoelectron current, and indicating a condition of quality based on the generated signal that is indicative of photoelectron current.

In a further aspect, the present invention is directed to a method for performing quality inspections on a test surface comprising the steps of producing optical radiation having a continuum spectrum, selecting a narrow band of wavelengths from the continuum and directing the selected spectrum band to the test surface, detecting a current of photoelectrons emitted from the test surface, generating a signal indicative of photoelectron current, and indicating a condition of quality based on the generated signal that is indicative of photoelectron current.

BRIEF DESCRIPTION OF THE DRAWINGS

The foregoing features of the present invention will become more readily apparent and may be understood by referring to the following detailed description of an illustrative embodiment of the present invention, taken in conjunction with the accompanying drawings, in which.

DETAILED DESCRIPTION OF THE INVENTION

The present invention provides several improvements to the operation of a conventional Optically Stimulated Electron Emission (OSEE) contamination monitor. OSEE monitors are generally described in U.S. Pat. No. 5,393,980 entitled "Quality Monitor And Monitoring Technique Employing Optically Stimulated Electron Emission," the disclosure of which is herein incorporated by reference as if set forth in its entirety.

Figure 1:
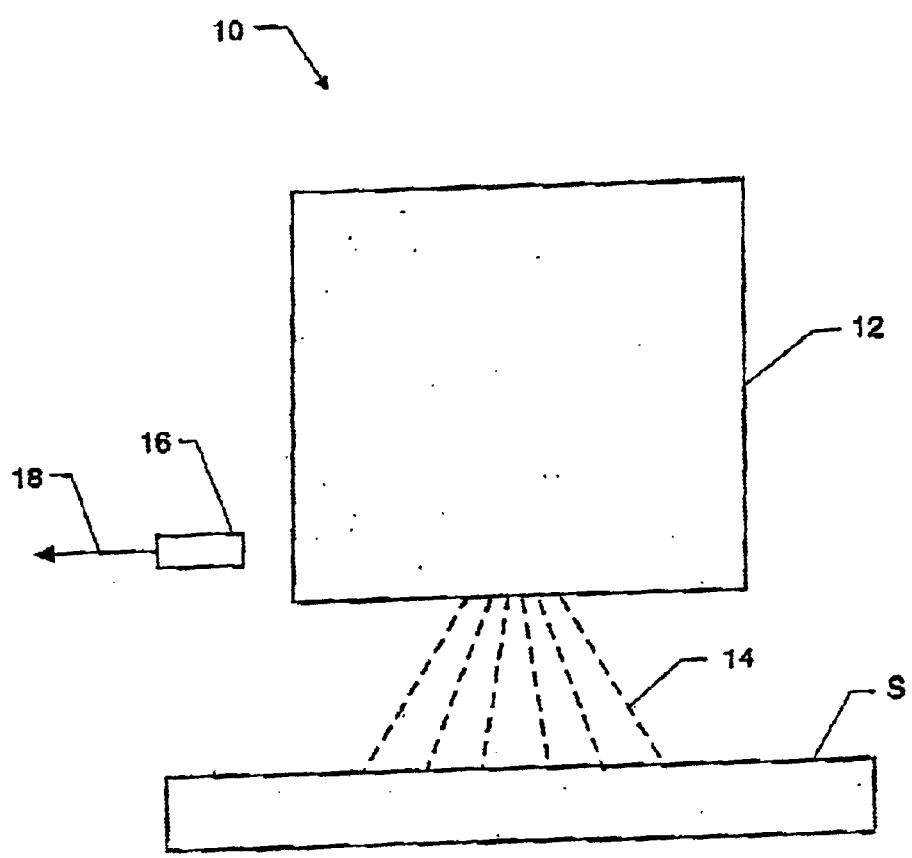
FIG. 1 is a block diagram of a monitor apparatus of the present invention.

Referring now to the drawings, in which like reference numerals and labels identify similar or identical elements throughout the several views, the monitor apparatus 10 of the present invention is shown in FIG. 1. In one embodiment, the monitor apparatus 10 generally comprises multi-state device 12 which includes components that effect production of optical radiation having a plurality of different spectrum lines, selection of at least one of the spectrum lines, and direction of selected spectrum lines 14 to the test surface S. In one embodiment, the components of multi-state device 12 that produce the optical radiation comprise a monochromatic incident light source. In one embodiment, the components of device 12 that produce the optical radiation comprise a tunable ultraviolet laser to produce different spectrum lines. In such an embodiment, each wavelength to which the laser is tuned can correspond to a particular state (or operational state) of multi-state device 12. In another embodiment, the components of device 12 that produce the spectrum lines of optical radiation comprise a dye laser. In another embodiment, the components of device 12 that produce the optical radiation comprise an excimer lamp. In another embodiment, the components of device 12 that produce the optical radiation comprise a series of Microhollow Cathode Discharge (MCD) lamps. In such a configuration, each MCD has a particular wavelength and is successively turned on and off. In another embodiment, the components of device 12 that produce the optical radiation comprise a low-pressure mercury vapor lamp. In a further embodiment, the components of device 12 that produce the optical radiation comprise a continuum spectral source such as a deuterium lamp. Other known components for producing optical radiation could also be used.

Apparatus 10 further includes circuit 16 for detecting a current of photoelectrons (not shown) emitted from the test surface S and generating a signal 18 that is indicative of photoelectron current and indicative of quality. Signal 18 can be inputted into external or peripheral equipment (not shown). Circuit 16 includes circuitry that allows the condition of quality to be based on a combination of the signals indicative of photoelectron current from each state of multi-state device 12. Circuit 16 can include collector circuitry for collecting the photoelectron current, additional circuitry for positively biasing the collector with respect to the test surface S, and circuitry for negatively biasing the collector with respect to the test surface S to replace charges removed (as photoelectron current) from the test surface S by the previously positively biased collector. Such circuitry and components are also described in U.S. Pat. No. 5,393,980.

Figure 2:
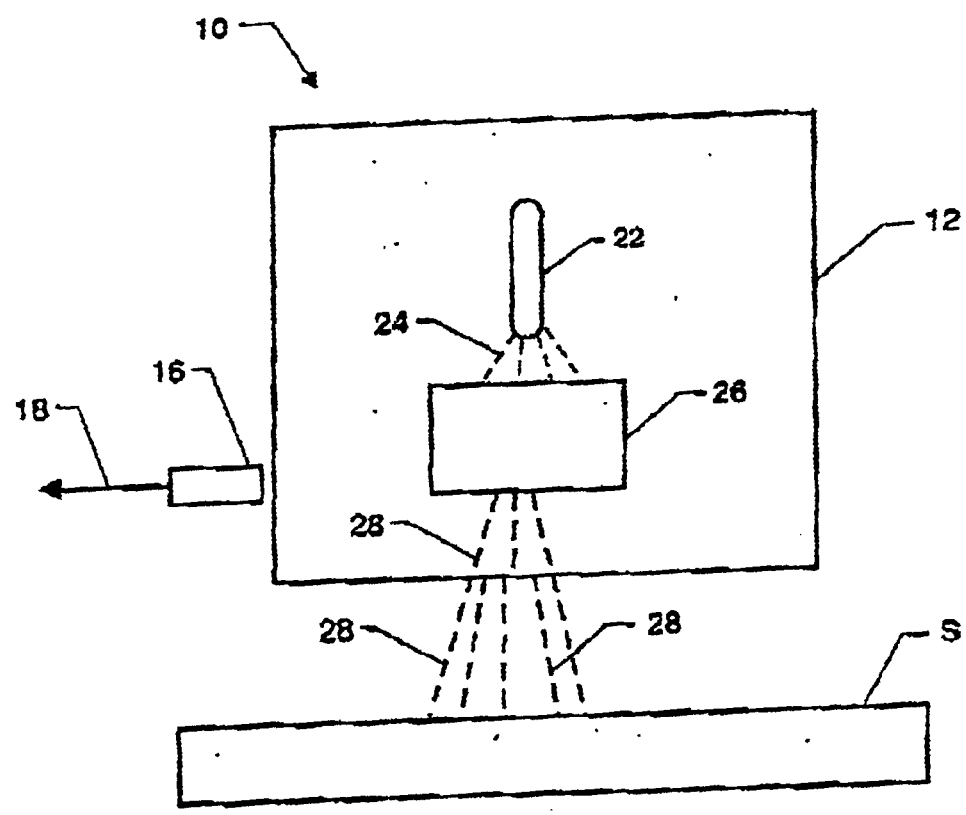
FIG. 2 is a schematic diagram of a monitor apparatus in accordance with one embodiment of the present invention.

Referring to FIG. 2, there is shown one embodiment of apparatus 10. In such an embodiment, multi-state device 12 comprises optical radiation source 22 that emits optical radiation 24. Device 12 further includes a filtering device 26. Filtering device 26 filters the optical radiation 24 directed to the test surface S. The filtering device 26 is configured to have a plurality of filtering sections (not shown) wherein each filtering section can comprise a filter that allows at least one particular spectrum line 28 to pass therethrough. In such an embodiment, a first one of the plurality of filtering sections allows only a first spectrum line to pass therethrough, a second one of the filtering sections allows only a second spectrum line to pass therethrough, and a third one of the plurality of filtering sections allows only the first and second spectrum lines to pass therethrough. In such an embodiment, filtering device 26 has a first state that allows only the first one of the filtering section filters to be activated, a second state that allows only the second one of the filtering section filters to be activated, and a third state that allows only the third one of the filtering sections to be activated. Filtering device 26 includes a fourth filtering section that allows all spectrum lines of optical radiation to pass to the test surface S and a fourth state that allows only the fourth filtering section to be activated.

In one embodiment, each filtering section comprises a diffraction grating. In another embodiment, each of the filtering sections comprises a dielectric filter that has particular optical properties.

The particular spectrum lines that are allowed to pass to the test surface S can depend upon the particular test surface S in question. For example, if the test surface is metal, then suitable spectrum lines such as the 185 nm spectrum line and the 254 nm spectrum line, for example from a low pressure mercury vapor lamp, may be used.

Referring to FIGS. 1 and 2, apparatus 10 may include other devices, components and structures, for example, those that are described in the aforementioned U.S. Pat. No. 5,393,980.

In one embodiment of the invention, apparatus 10 comprises the light tube of the well known hand-held 3 rd generation OSEE, a filter case having the aforesaid plurality of filtering sections, and a filter-selection device that allows for selection of a particular one of the filtering sections and the positioning of the selected filtering section within the light path of the tube.

The mode of operation of apparatus 10 relies on the basic shape of the photoelectron emission spectrum in the wavelength range for surface emissions. For example, if the sample under test is a metal surface and apparatus 10 utilizes a low-pressure mercury vapor lamp, apparatus 10 can use two wavelengths (e.g. 185 nm and 254 nm) that generate OSEE on most metal surfaces and also facilitate distinguishing between oxidation and contamination and distinguishing among different contaminant species. Thus, if oxidation alters the work function of the sample under test and hence, alters the wavelength of the photoelectric cutoff of the sample under test as well, the decrease in the response to the 254 nm line of the mercury spectrum will be relatively larger than the decrease in response to the 185 nm line. On the other hand, if contamination occurs, the relative decrease in the signal for the 254 nm spectrum line will be similar to that of the 185 nm line. If the contaminant is known and the absorption spectrum for that contaminant is known, the expected ratios of decrease for a contamination spot can be calculated in advance. Thus, one can discriminate between a contamination spot and an oxidation spot on an otherwise clean piece of material by examining the ratios of decrease in signal for the two wavelengths of light. Likewise, if the absorption spectrum for several different contaminants is known, the expected ratios of decrease or increase for a contamination spot can be calculated in advance. Thus one can discriminate among a variety of contaminant species by examining the ratios of the decrease or increase in signal for the two wavelengths of light. A simple check on the validity of the measurements can be made by removing the filters from the light path and making the measurement for the sum of the two wavelengths, having corrected for filter responses which can be obtained independently with radiometer measurements. The present invention uses these related calculations to discriminate between oxidation and contamination using OSEE and/or to discriminate among a variety of contaminant species.

Thus, the present invention allows for a plurality of OSEE measurements on a given surface at different wavelengths of optical radiation (i.e. incident light) as well as the combined wavelengths so that the comparison of the plurality of measurements can be used to distinguish between surface contamination and corrosion and to discriminate among a variety of contaminant species. As a result, the present invention provides at least the following advantages:

a) relatively high sensitivity to clean substrates with small contaminant amounts;

b) immediate generation of results;

c) discrimination between oxidation and contamination over extended surfaces;

d) discrimination among a variety of contaminant species; and e) elimination of the need for physical contact between the sample under test and the monitoring equipment.

The present invention is a particularly useful tool in manufacturing when it is necessary to place coatings or adhesives on steel surfaces. Specifically, the present invention can significantly improve the inspection of bonding surfaces immediately prior to the coating application and reduce the overall time for such inspection.

The principles, preferred embodiments, and modes of operation of the present invention have been described in the foregoing specification. The invention which is intended to be protected herein should not, however, be construed as limited to the particular forms disclosed, as these are to be regarded as illustrative rather than restrictive. Variations or changes may be made by those skilled in the art without departing from the spirit of the invention. Accordingly, the foregoing detailed description should be considered exemplary in nature and not limit the scope and spirit of the invention as set forth in the attached claims.

What is claimed is:

1. An apparatus for performing quality inspections on a test surface comprising:

a device for producing optical radiation having a plurality of different spectrum lines, selecting at least one of the spectrum lines, and directing the selected spectrum line to the test surface;

circuitry for detecting a current of photoelectrons emitted from the test surface, generating a signal indicative of photoelectron current, and indicating a condition of quality based on the generated signal indicative of photoelectron current;

the indicating circuitry comprising an arrangement for evaluating the generated signal to thus distinguish between at least one of:

surface contamination and oxidation; and different species of contaminants.

2. The apparatus according to claim 1 wherein the device comprises an ultraviolet optical radiation source.

3. The apparatus according to claim 2 wherein the ultraviolet optical radiation source comprises an ultraviolet laser.

4. The apparatus according to claim 3 wherein the laser comprises a tunable laser.

5. The apparatus according to claim 2 wherein the ultraviolet optical radiation source comprises an excimer lamp.

6. An apparatus for performing quality inspections on a test surface comprising:

a device for producing optical radiation having a plurality of different spectrum lines, selecting at least one of the spectrum lines, and directing the selected spectrum line to the test surface;

circuitry for detecting a current of photoelectrons emitted from the test surface, generating a signal indicative of photoelectron current, and indicating a condition of quality based on the generated signal indicative of photoelectron current;

the device comprising an ultraviolet optical radiation source; and the ultraviolet optical radiation source comprising a plurality of Microhollow Cathode Discharge lamps.

7. The apparatus according to claim 1 wherein the selecting device comprises a filtering device that filters the optical radiation directed to the test surface.

8. The apparatus according to claim 7 wherein the filtering device comprises a plurality of filtering sections, each filtering section allowing at least one particular spectrum line to pass therethrough.

9. The apparatus according to claim 8 wherein a first one of the plurality of filtering sections allows only a first spectrum line to pass through, a second one of the filtering sections allows only a second spectrum line to pass therethrough, and a third one of the plurality of filtering sections allows only the first and second spectrum lines to pass therethrough.

10. An apparatus for performing quality inspections on a test surface comprising:

a device for producing optical radiation having a plurality of different spectrum lines, selecting at least one of the spectrum lines, and directing the selected spectrum line to the test surface;

circuitry for detecting a current of photoelectrons emitted from the test surface, generating a signal indicative of photoelectron current, and indicating a condition of quality based on the generated signal indicative of photoelectron current;

the selecting device comprising filtering device that filters the optical radiation directed to the test surface;

the filtering device comprising a plurality of filtering sections, each filtering section allowing at least one particular spectrum line to pass therethrough;

a first one of he plurality of filtering sections allowing only a first spectrum line to pass therethrough, a second one of the filtering sections allowing only a second spectrum line to pass therethrough, and a third one of the plurality of filtering sections allowing only the first and second spectrum lines to pass therethrough; and the filtering device having a first state that enables only the first one of the filtering sections to filter the optical radiation, a second state that enables only the second one of the filtering section to filter the optical radiation, and a third state that enables only the third filtering section to filter the optical radiation.

11. The apparatus according to claim 10 wherein a fourth one of the plurality of filtering sections allows all spectrum lines to pass to the test surface, the filtering device further including a fourth state that allows only the fourth filtering section to filter the optical radiation.

12. The apparatus according to claim 8 wherein each of the filtering sections comprises diffraction gratings.

13. An apparatus for performing quality inspections on a test surface comprising:

a device for producing optical radiation having a plurality of different spectrum lines, selecting a least one of the spectrum lines, and directing selected spectrum line to the test surface;

circuitry for detecting a current of photoelectrons emitted from the test surface, generating a signal indicative of photoelectron current, and indicating a condition of quality based on the generated signal indicative of photoelectron current;

the selecting device comprising a filtering device that filters the optical radiation directed to the test surface;

the filtering device comprising a plurality of filtering sections, each filtering section allowing at least one particular spectrum line to pass therethrough; and each of the filtering sections comprising dielectric filter.

14. The apparatus according to claim 1 wherein the detecting circuitry includes a collector for collecting the photoelectron current and means for positively biasing the collector with respect to the test surface.

15. The apparatus according to claim 14 further comprising means for negatively biasing the collector with respect to the test surface to replace charges removed as photoelectron current from the test surface by the previously positively biased collector.

16. An apparatus for performing quality inspections on a test surface comprising:

means for producing optical radiation having a plurality of different spectrum lines, selecting at least one of the spectrum lines, and directing the selected spectrum line to the test surface; a means for detecting a current of photoelectrons emitted from the test surface, generating a signal indicative of photoelectron current, and indicating a condition of quality based on the generated signal indicative of photoelectron current; and the means for indicating a condition of quality being capable of distinguishing between;

surface contamination;

surface corrosion; and different species of contaminants.

17. An apparatus for performing quality inspections on a test surface based on optically stimulated emission of electrons comprising:

an optical radiation source for producing optical radiation having a plurality different spectrum lines;

a selection device for selecting at least one of the spectrum lines and directing the selected spectrum line to the test surface;

circuitry for detecting a current of photoelectrons emitted from the test surface and generating a signal indicative of the detected photoelectron current;

circuitry for indicating a condition of quality based on the generated sigal indicative of photoelectron current; and wherein the circuitry for indicating a condition of quality comprises circuitry for evaluating the generated signal indicative of photoelectron current to thereby discriminate between at least one of:

surface contamination and corrosion; and different species of contaminates.

18. An apparatus for performing quality inspections on a test surface comprising:

a multi-state device for producing optical radiation in the direction of the test surface, the optical radiation defining a particular spectrum line that corresponds to a particular state of the device wherein each state of the device effects generation of at least one particular spectrum line;

circuitry for successively configuring the device into different states;

additional circuitry for detecting a current of photoelectrons emitted from the test surface, generating a signal indicative of photoelectron current, and indicating a condition of quality based on the generated signal indicative of photoelectron currents; and the indicating circuitry comprising an arrangement for evaluating the generated signal to thus distinguish between at least one of:

surface contamination and corrosion; and different species of contaminants.

19. The apparatus according to claim 18 wherein the additional circuitry detects a current of photoelectrons emitted from the test surface for each state of the multi-state device, the additional circuitry including circuitry for combining the detected current of photoelectrons emitted from the test surface for each state of the multi-state device into a single detection signal, the additional circuitry being configured so that the indicated condition of quality is based upon the single detection signal.

20. An apparatus for performing quality inspections on a test surface comprising:

means for producing optical radiation having a continuum spectrum, selecting a band of at least one wavelength from the continuum, and directing the selected band to the test surface;

means for detecting a current of photoelectrons emitted from the test surface, generating a signal indicative of photoelectron current, and indicating a condition of quality based on the generated signal indicative of photoelectron current; and the means for indicating a condition of quality comprising means for distinguishing between at least one of:

surface contamination;

surface oxidation; and different species of contaminants.

21. An apparatus for performing quality inspections on a teat surface comprising:

means for producing optical radiation having a continuum spectrum, selecting a band of at least one wavelength from the continuum, and directing the selected band to the test surface;

means for detecting a current of photoelectrons emitted from the test surface, generating a signal indicative of photoelectron current, and indicating a condition of quality based on the generated signal indicative of photoelectron current; and the means for producing optical radiation comprising a deuterium lamp.

22. The apparatus according to claim 20 wherein the selecting means comprises a filtering device that filters the optical radiation directed to the test surface.

23. The apparatus according to claim 22 wherein the filtering device comprises a plurality of filtering sections, each filtering section allowing at least one particular spectrum band to pass therethrough.

24. The apparatus according to claim 23 wherein a first one of the plurality of filtering sections allows only a first spectrum band to pass therethrough, a second one of the filtering sections allows only a second spectrum band to pass therethrough, and a third one of the plurality of filtering sections allows only the first and second spectrum band to pass therethrough.

25. An apparatus for perfuming quality inspections on a test surface comprising:

means for producing optical radiation having a continuum spectrum, selecting a band of at least one wavelength from the continuum, and directing the selected band to the test surface;

means for detecting a current of photoelectrons emitted from the test surface, generating a signal indicative of photoelectron current, and indicating a condition of quality based on the generated signal indicative of photoelectron current;

the selecting means comprising a filtering device that filters the optical radiation directed to the test surface;

the filtering device comprising a plurality of filtering sections, each filtering section allowing at least one particular spectrum band to pass therethrough;

a first one of the plurality of filtering sections allowing only a first spectrum band to pass therethrough, a second one of the filtering sections allowing only a second spectrum band to pass therethrough, and a third one of the plurality of filtering sections allowing only the first and second spectrum bands to pass therethrough; and the filtering device having a first state that enables only the first one of the filtering sections to filter the optical radiation, a second state that enables only the second one of the filtering section to filter the optical radiation, and a third state that enables only the third filtering section to filter the optical radiation.

26. The apparatus according to claim 25 wherein a fourth one of the plurality of filtering sections allows all spectrum bands to pass to the test surface, the filtering device further including a fourth state that allows only the fourth filtering section to filter the optical radiation.

27. The apparatus according to claim 23 wherein each of the filtering sections comprises diffraction gratings.

28. An apparatus for performing quality inspections on a test surface comprising:

means for producing optical radiation having a continuum spectrum, selecting a band of at least one wavelength from the continuum, and directing the selected band to the test surface;

means for detecting a current of photoelectrons emitted from the test surface, generating a signal indicative of photoelectron current, and indicating a condition of quality based on the generated signal indicative of photoelectron current;

the selecting means comprising a plurality of filtering device that filters the optical radiation directed to the test surface;

the filtering device comprising a plurality of filtering sections, each filtering section allowing at least one particular band to pass therethrough; and each of the filtering sections comprising a dielectric filter.

29. The apparatus according to claim 20 wherein the detecting means includes a collector for collecting the photoelectron current and means for positively biasing the collector with respect to the test surface.

30. The apparatus according to claim 29 further comprising means for negatively biasing the collector with respect to the test surface to replace charges removed as photoelectron current from the test surface by the previously positively biased collector.

31. The apparatus according to claim 27 wherein each of the diffraction gratings comprise a slit, thereby permitting the at least one particular spectrum band to pass therethrough.

* * * * *